(12) United States Patent
Ingvast et al.

(10) Patent No.: US 10,786,022 B2
(45) Date of Patent: Sep. 29, 2020

(54) CONTROL SYSTEM FOR A STRENGTHENING GLOVE

(71) Applicant: Bioservo Technologies Aktiebolag, Kista (SE)

(72) Inventors: Johan Ingvast, Åkersberga (SE); Martin Oskar Gustaf Ewaldsson, Sigtuna (SE)

(73) Assignee: BIOSERVO TECHNOLOGIES AKTIEBOLAG, Kista (SE)

( * ) Notice: Subject to any disclaimer, the term of this patent is extended or adjusted under 35 U.S.C. 154(b) by 23 days.

(21) Appl. No.: 15/569,306

(22) PCT Filed: Apr. 27, 2016

(86) PCT No.: PCT/EP2016/059399
§ 371 (c)(1),
(2) Date: Oct. 25, 2017

(87) PCT Pub. No.: WO2016/174083
PCT Pub. Date: Nov. 3, 2016

(65) Prior Publication Data
US 2018/0116310 A1    May 3, 2018

(30) Foreign Application Priority Data
Apr. 29, 2015 (SE) ...................... 1550529

(51) Int. Cl.
*A41D 19/015* (2006.01)
*B25J 9/00* (2006.01)
(Continued)

(52) U.S. Cl.
CPC ........ *A41D 19/01582* (2013.01); *A61B 5/225* (2013.01); *A61B 5/6806* (2013.01);
(Continued)

(58) Field of Classification Search
CPC ... A41D 19/00; A41D 19/01547; A61F 5/013; A63B 23/16
See application file for complete search history.

(56) References Cited

U.S. PATENT DOCUMENTS 5,143,505 A * 9/1992 Burdea ................. A61F 5/0118
244/234
5,631,861 A * 5/1997 Kramer ................... G06F 3/011
414/5
(Continued)

FOREIGN PATENT DOCUMENTS

EP    2417941 A1    2/2012

OTHER PUBLICATIONS

Murakami, K. et al., "A Decision Method for Placement of Tactile Elements on a Sensor Glove for the Recognition of Grasp Types," IEEE/ASME Transactions on Mechatronics, vol. 15, No. 1, Feb. 1, 2010, pp. 157-162.
(Continued)

*Primary Examiner* — David A. Rogers
(74) *Attorney, Agent, or Firm* — Tucker Ellis LLP

(57) ABSTRACT

Control system (200) for a strengthening glove (100) with fingers (101-105), comprising a force detecting sensor means (210) for detecting, at different measurement locations (211-218) on the palm side (106) of said glove fingers, a respective force between a finger (11-15) and a contact surface, further arranged to impart a force to respective glove fingers, bending them towards a gripping position, further arranged to read measurement values from the strengthening feedback loop based upon the measurement values. The invention is characterised in that a predetermined pattern is detected, comprising certain measurement values, in that, when the said pattern is not detected and the actuating means are controlled according to a first program, and further when the said pattern is detected, they are
(Continued)

controlled according to a second program, which first and second programs are different.

20 Claims, 5 Drawing Sheets

(51) Int. Cl.
*A61B 5/22* (2006.01)
*A61H 1/02* (2006.01)
*A61B 5/00* (2006.01)

(52) U.S. Cl.
CPC .......... *A61H 1/0288* (2013.01); *B25J 9/0006* (2013.01); *A61H 2201/1215* (2013.01); *A61H 2201/149* (2013.01); *A61H 2201/165* (2013.01); *A61H 2201/1635* (2013.01); *A61H 2201/5007* (2013.01)

(56) References Cited

U.S. PATENT DOCUMENTS

| | | | | |
|---|---|---|---|---|
| 5,676,157 | A * | 10/1997 | Kramer | A61B 5/103 600/595 |
| 5,771,492 | A * | 6/1998 | Cozza | A63B 69/3608 2/161.2 |
| 5,845,540 | A * | 12/1998 | Rosheim | B25J 3/04 74/490.05 |
| 6,016,103 | A * | 1/2000 | Leavitt | G08B 21/06 340/575 |
| 6,042,555 | A * | 3/2000 | Kramer | A61B 5/225 600/595 |
| 6,452,584 | B1 * | 9/2002 | Walker | G06F 3/014 345/158 |
| 6,681,638 | B2 * | 1/2004 | Kazerooni | B65G 43/00 254/266 |
| 7,562,572 | B2 * | 7/2009 | You | G01L 1/205 73/379.03 |
| 8,029,414 | B2 | 10/2011 | Ingvast | |
| 8,467,903 | B2 * | 6/2013 | Ihrke | B25J 9/104 700/245 |
| 8,574,178 | B2 * | 11/2013 | Tong | A61H 1/0285 601/40 |
| 8,998,831 | B2 * | 4/2015 | Sankai | A61B 5/04888 601/40 |
| 9,067,325 | B2 * | 6/2015 | Ihrke | B25J 15/08 |
| 9,120,220 | B2 * | 9/2015 | Bergelin | B25J 9/0006 |
| 9,345,424 | B2 * | 5/2016 | Wang | A61B 5/103 |
| 9,468,847 | B2 * | 10/2016 | Bekri | A63F 13/285 |
| 9,566,173 | B2 * | 2/2017 | Ryu | G06F 3/011 |
| 9,668,931 | B2 * | 6/2017 | Nussbaum | A61H 23/02 |
| 9,878,452 | B2 * | 1/2018 | Davis | B25J 9/104 |
| 9,910,491 | B2 * | 3/2018 | Mutz | B07C 7/005 |
| 9,983,669 | B2 * | 5/2018 | Luo | G06F 3/014 |
| 10,466,784 | B2 * | 11/2019 | Cohen | A61F 5/013 |
| 2002/0178830 | A1 * | 12/2002 | Kazerooni | B65G 43/00 73/760 |
| 2010/0041521 | A1 * | 2/2010 | Ingvast | A61H 1/0288 482/49 |
| 2011/0071664 | A1 * | 3/2011 | Linn | B25J 9/0006 700/213 |
| 2011/0071678 | A1 * | 3/2011 | Ihrke | B25J 9/104 700/258 |
| 2013/0197399 | A1 * | 8/2013 | Montgomery | A61B 5/1121 600/595 |
| 2013/0226350 | A1 | 8/2013 | Bergelin | |
| 2017/0042704 | A1 * | 2/2017 | Ryu | A61F 2/68 |

OTHER PUBLICATIONS

International Search Report from corresponding International Application No. PCT/EP2016/059399, dated Jul. 26, 2016.
International Preliminary Report on Patentability from corresponding International Application No. PCT/EP2016/059399, dated Apr. 18, 2017.
Hasegawa, Yasuhisa, et al., "Pinching Force Accuracy Affected by Thumb Sensation in Human Force Augmentation", IEEE/RSJ International Conference on Intelligent Robots and Systems, Oct. 2012, Portugal, pp. 3943-3948.

* cited by examiner

CONTROL SYSTEM FOR A STRENGTHENING GLOVE

The present invention relates to a feedback control system for a strengthening glove, in other words a glove arranged to be worn by a human hand and used for strengthening a gripping movement executed by one or more fingers of the hand. The invention also relates to such a glove in itself, as well as to a method for operating such a strengthening glove.

Such strengthening gloves are known, using different operating principles, such as arranging individual driving units on each finger to be strengthened or by using wires or cables, such as artificial tendons, in order to apply pushing and/or pulling forces onto particular points on each finger to be strengthened. For instance, electric or pneumatic driving mechanisms may be employed.

One example of such a glove is described in U.S. Pat. No. 8,029,414 B2, using artificial tendons fastened to strengthened fingers and driven by a central control unit in turn applying pulling forces to the tendons.

Such a glove operates to offer general strengthening of the movements of the human hand wearing the glove. For instance, when the human hand grips an object, the gripping force applied by the human user is amplified so as to strengthen the grip.

A problem when using such a glove is that particular actions require particular aid. For instance, when carrying an object it may be difficult for a user to maintain a sufficiently strong grip over time even if aided by the strengthening glove. This is, for instance, the case for many patient groups with muscular or nerve damage.

US 2013226350 A1 discloses a strengthening glove with specific gripping features, initiated using a separate control device.

The present invention solves these problems by providing a control system and a strengthening glove using which different control programs are initiated using input from the same sensor locations that are used in a feedback loop in order to perform the strengthening action of the glove, as well as a method implementing such functionality. Hence, the invention relates to a control system for a strengthening glove with at least one glove finger, which control system is arranged to strengthen a gripping movement performed by a human hand wearing the glove, which control system comprises at least one force detecting sensor means arranged to detect, in at least two different measurement locations on the palm side of said at least one glove finger, a respective force between a respective human finger wearing the respective glove finger and a respective contact surface onto which said gripping movement is applied, which control system further comprises at least one actuating means arranged to impart a force to a respective one of said glove fingers, so that the corresponding human finger wearing the glove finger in question is bent towards a gripping position, which control system further comprises a control device, arranged to read a respective measurement value from the sensor means for each of said measurement locations, and to control the respective force applied by said at least one actuating means using a force strengthening feedback loop based upon the said measurement values, which control system is characterised in that the control device is arranged to detect a predetermined pattern comprising such measurement values, in that the control device is arranged so that, in a first control state when the said pattern is not detected, it controls the actuating means according to a first program, and so that, when the said pattern is detected in said first control state, it switches to a second control state in which it controls the actuating means according to a second program, and in that the first and second programs are different.

The invention also relates to a method for operating a strengthening glove with at least one glove finger, which glove is arranged to strengthen a gripping movement performed by a human hand wearing the glove, which glove comprises at least one force detecting sensor means arranged to detect, in at least two different measurement locations on the palm side of said at least one glove finger, a respective force between a respective human finger wearing the respective glove finger and a respective contact surface onto which said gripping movement is applied, which glove further comprises at least one actuating means arranged to impart a force to a respective one of said glove fingers, so that the corresponding human finger wearing the glove finger in question is bent towards a gripping position, which glove further comprises a control device, arranged to read a respective measurement value from the sensor means for each of said measurement locations and to control the respective force applied by said at least one actuating means using a force strengthening feedback loop based upon the said measurement values, which method is characterised in that the method comprises the steps of a) detecting a predetermined pattern comprising such measurement values; b) in a first control state when the said pattern is not detected, causing the control device to control the actuating means according to a first program; and c) when the said pattern is detected in said first control state, causing the control device to switch to a second control state in which it controls the actuating means according to a second program, wherein the first and second programs are different.

In the following, the invention will be described in detail, with reference to exemplifying embodiments of the invention and to the enclosed drawings, wherein.

Figure 3A:
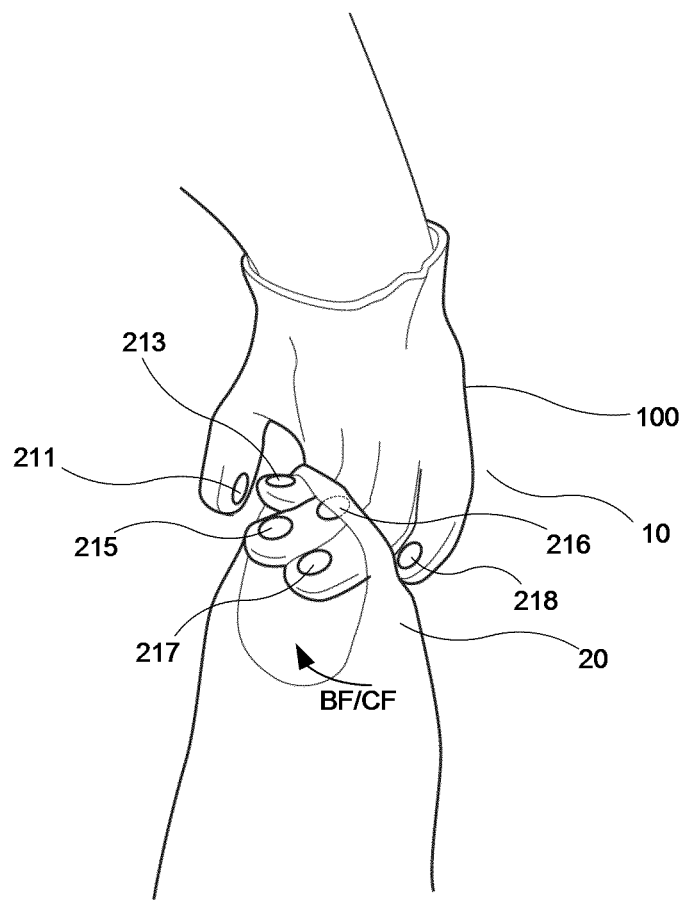
Figure 3B:
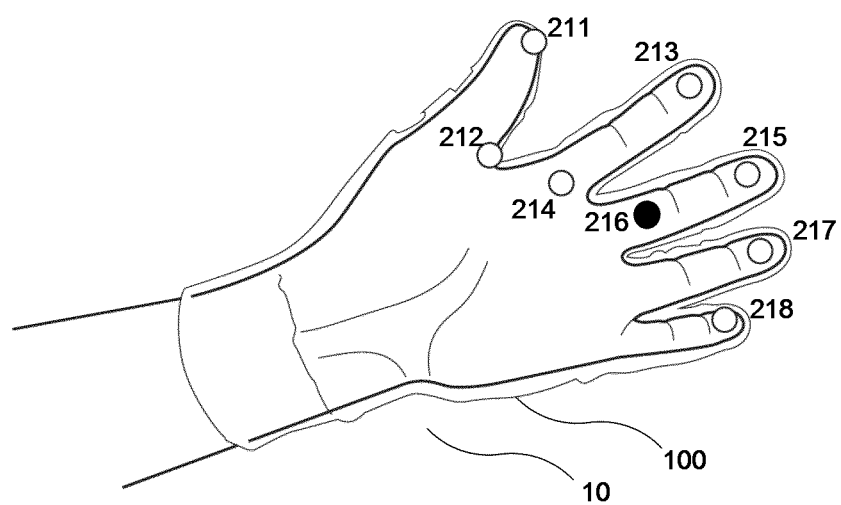
Figure 4A:
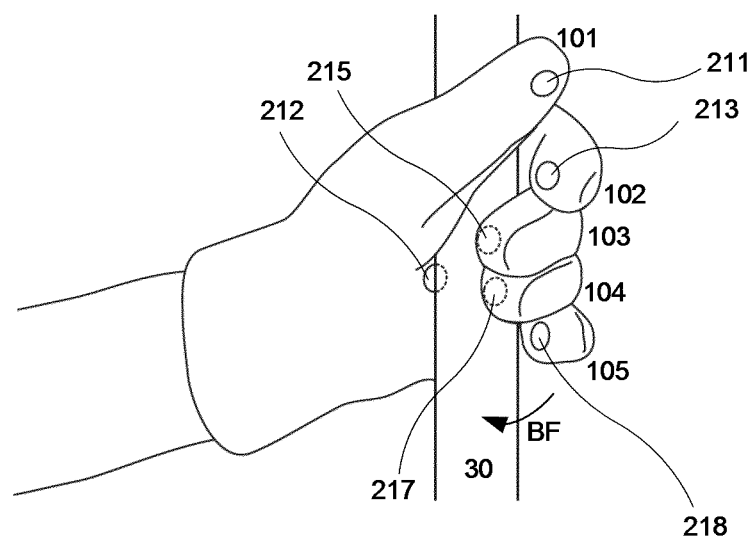
Figure 4B:
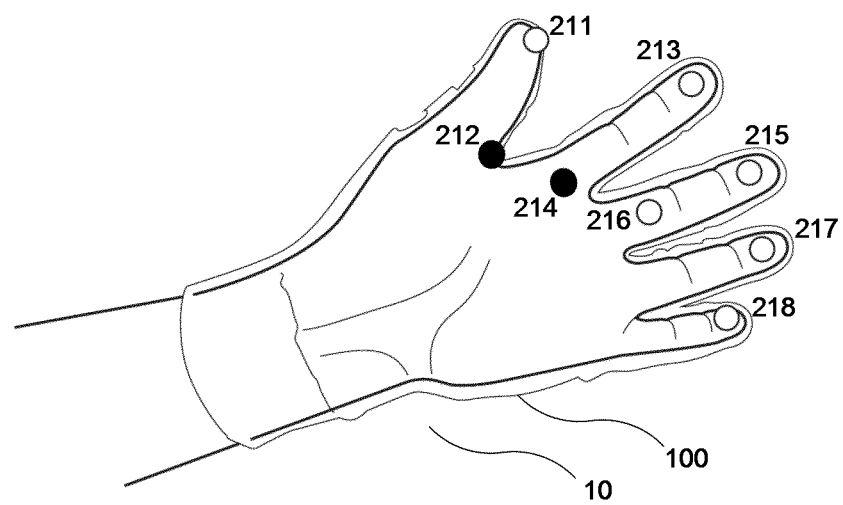
Figure 4C:
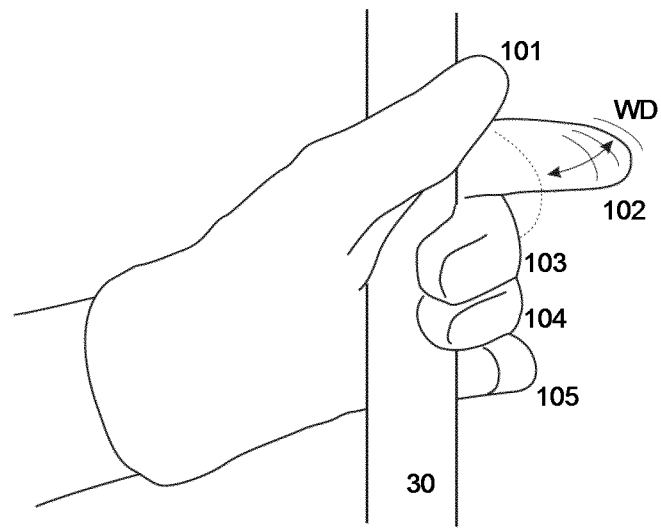
Figure 5:
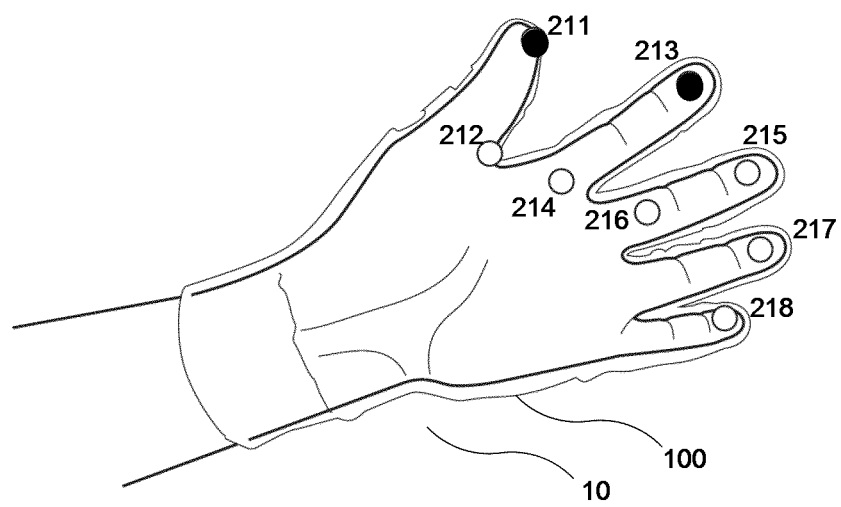
Figure 6:
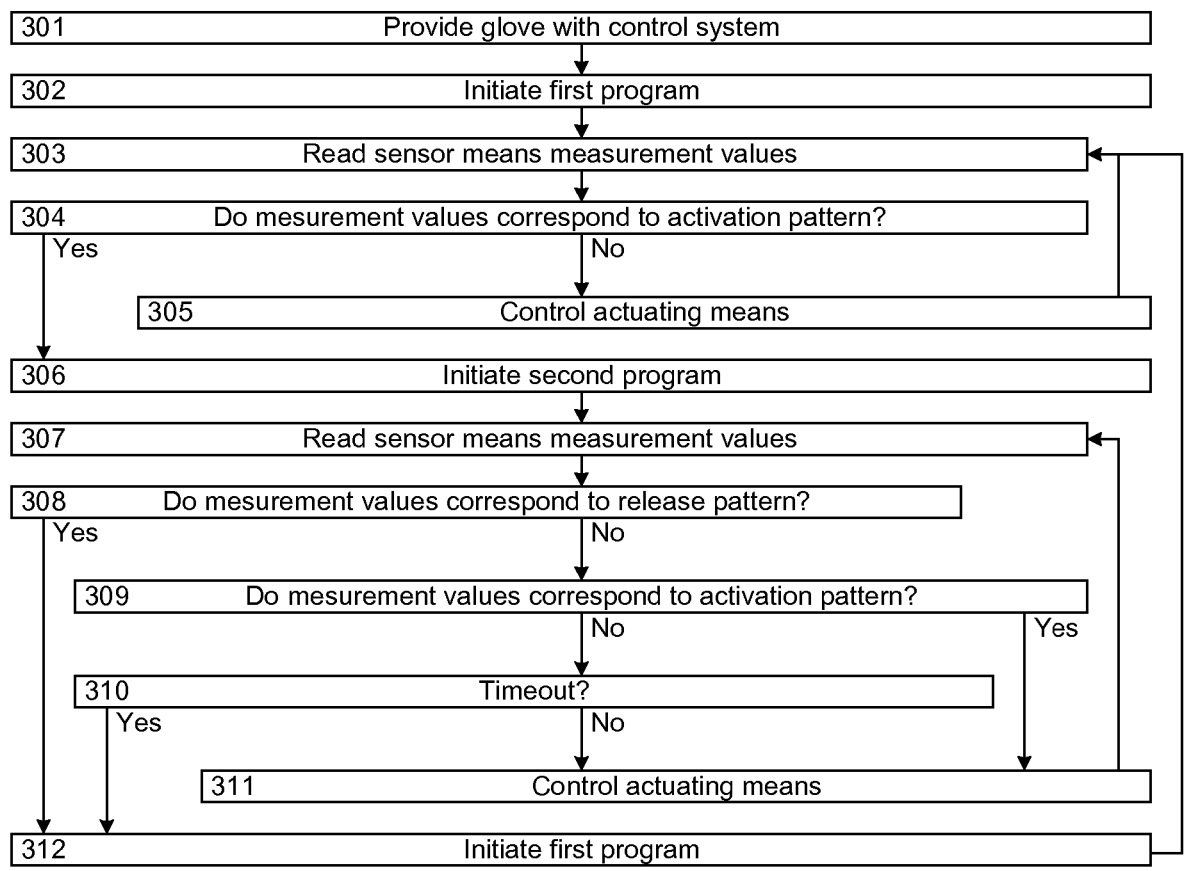

FIG. 3*a* is a perspective view of a glove according to the invention in a first mode of operation;

FIG. 3*b* is a perspective view of the glove of FIG. 3*a*, further showing a pressure detection pattern;

FIG. 4*a* is a perspective view of a glove according to the invention in a second mode of operation;

FIG. 4*b* is a perspective view of the glove of FIG. 4*a*, further showing a pressure detection pattern;

FIG. 4*c* is a perspective view of the glove of FIG. 4*a*, further showing a release pressure detection pattern;

FIG. 5 is a perspective view of a glove according to the present invention, illustrating a release pressure detection pattern; and FIG. 6 is a flowchart illustrating a method according to the invention.

All figures share the same reference numerals for similar or corresponding parts.

Figure 1:
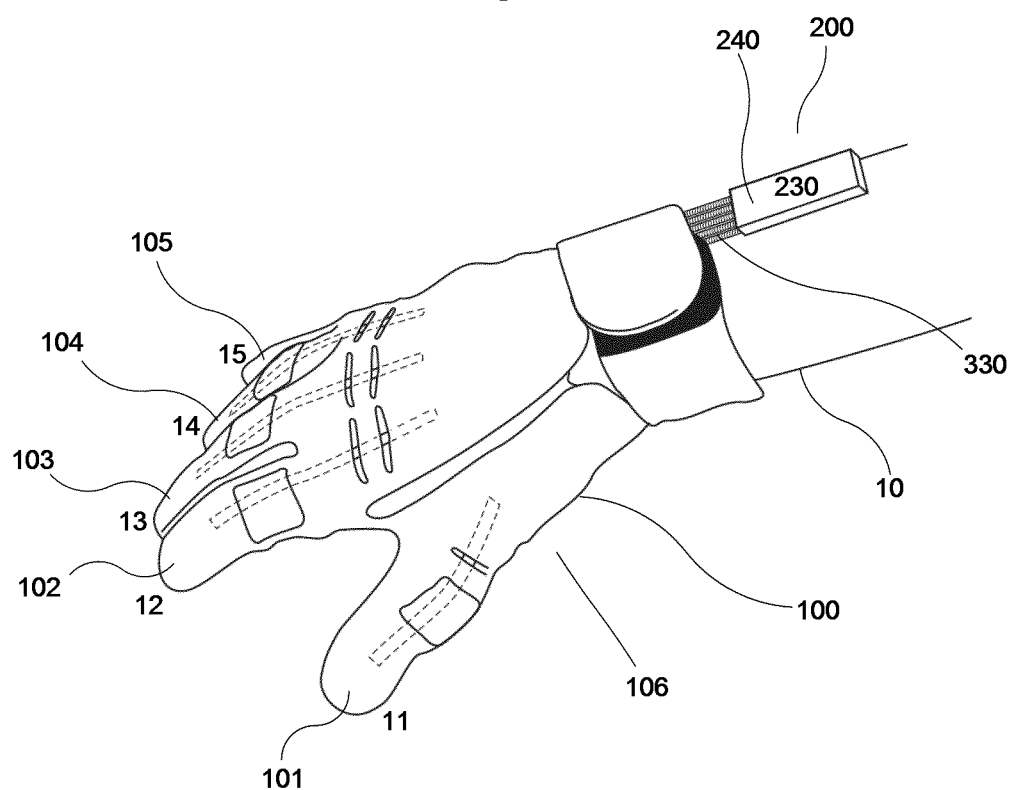
FIG. 1 is a perspective view of a strengthening glove according to the present invention, worn by a human hand and comprising a control system according to the present invention.
Figure 2:
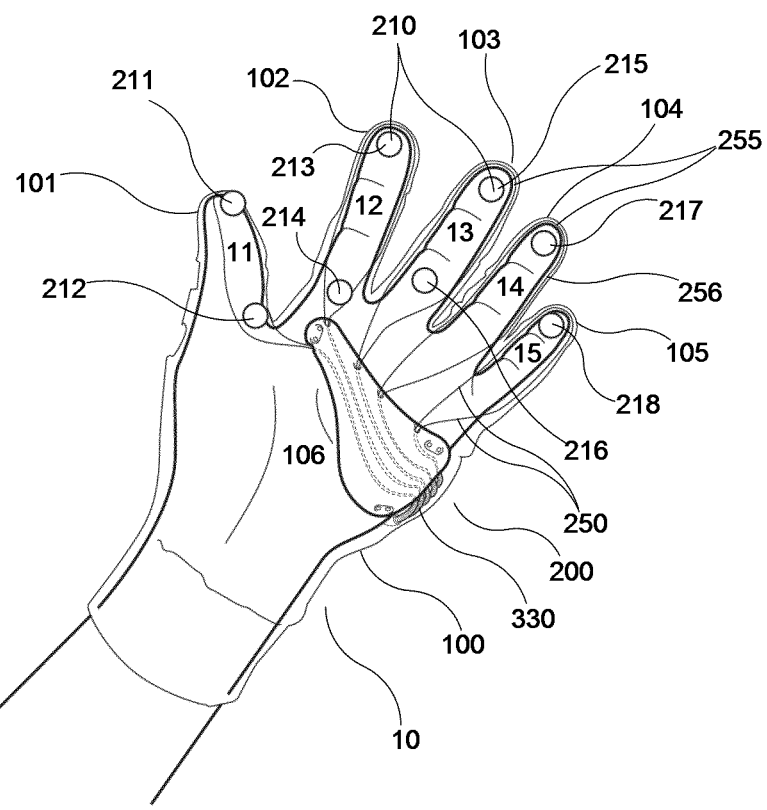
FIG. 2 illustrates the glove of FIG. 1, further showing sensor means.

FIG. 1 illustrates a human hand 10 wearing a strengthening glove 100 according to the invention. The strengthening glove 100 comprises a control system 200, also according to the present invention.

Furthermore, according to the invention the glove 100 comprises at least one glove finger. In FIG. 1, five glove fingers 101-105 are illustrated, for exemplifying purposes. The glove 100 is arranged to strengthen a gripping movement performed by the human hand 10 wearing the glove, in accordance with a feedback control program which may be conventional as such, for instance a program similar to the one described in U.S. Pat. No. 8,029,414.

In order for the glove 100 to be able to perform said control program, according to the invention the control system 200 comprises at least one force detecting sensor means 210 arranged to detect, in at least two different measurement locations 211-218 (see FIGS. 3b, 4b) on the palm 106 side of the said at least one glove fingers 101-105, a respective force between a respective human finger 11-15 wearing the respective glove finger 101-105 and a respective contact surface (see FIGS. 3a, 4a, 5a) onto which said gripping movement is applied, at the said respective measurement location 211-218. Hence, said measurement locations 211-218 may be arranged several on one single finger and/or on different fingers.

Furthermore to be able to perform said control program, the control system 200 also comprises at least one actuating means 240 (generally indicated in FIG. 1), arranged to impart a force to a respective one of said glove fingers 101-105, so that the corresponding human finger 11-15 wearing the glove finger 101-105 in question is bent towards a gripping position. In the figures, one and the same actuating means 240 is arranged to impart respective such forces to each one of the five fingers 101-105. However, it is realized that several actuating means may be used in parallel, for instance each operating on one finger each; and/or there may be less than five controlled glove fingers. More than one actuating means may also operate on one single particular finger, such as one actuating means being arranged to extend the finger and one being arranged to bend the finger in question. A combination of the above is also possible.

Furthermore, the control system 200 comprises a control device 230, in charge of the performance of the said program and connected to the actuating means 240. As such, the control device 230 comprises or has access to operating logic defining the said program. For instance, such logic may be implemented in mechanics comprised in the control device 230, but preferably the control device 230 comprises electronic hardware circuitry and/or, preferably, a digital processor programmed with a piece of software, arranged to implement the said control program. To be specific, the control device 230 is arranged to read a respective measurement value from the sensor means 210 for each of said measurement locations, and to control the respective force applied to each controlled finger 101-105 via the actuating means 240. The sensor means 210 is connected to the control device 230, for instance via electric cables (not shown in the figures).

The actuating means 240 may be conventional as such, for instance controlling finger 11-15 bending via tendons 250 (see below), pulling on the glove 100 fingers 101-105, by pulling the tendons 250 via an electrical motor.

Hence, the said control is performed using said control program, which comprises or is constituted by a force strengthening feedback loop, in turn based upon the said measurement values as input parameters. In other words, the control device 230 receives current force measurement values, performs calculations with these values as input parameters, and controls the actuating means 240 based upon output values of said calculations so as to achieve a force feedback program effectively strengthening or amplifying a gripping motion performed by the hand 10 wearing the glove 100. This type of feedback program is as such well known, for instance from U.S. Pat. No. 8,029,414 B2. Therefore, it is not described in closer detail herein.

However, according to the invention, the control device 230 is further arranged to detect a predetermined triggering pattern comprising at least a subset of the above described measurement values from the respective measurement locations 211-218 of the sensor means 210. Moreover, the control device 230 is arranged so that, when it is in a first control state and when the said pattern is not detected by the control device 230, it controls the actuating means 240 according to a first program, and so that, when the said pattern is detected by the control device 230 when it is in said first control state, it switches to a second control state in which it controls the actuating means 240 according to a second program, which first and second programs are different. Such a triggering pattern will in the following be denoted simply "pattern".

Hence, the control device 230 can operate in a "first" control state, in which it uses the first program, as well as one or several "second" control states, in which it uses a respective second program (see below for the case in which there may be more than one second programs). Hence, when the control device 230 switches to a certain first or second control state, the corresponding first or second program is immediately used by the control device 230 for control of said actuating means 240. The switching between said control states is triggered in a predictable manner by certain events, such as is exemplified herein below.

It is important to understand that the term "program" herein refers to the algorithm used to, based upon read sensor means 210 measurement values, calculate control data for controlling the actuating means 240, as opposed to the actual current control state fed to the actuating means 240. For example, merely the fact that a particular glove 100 finger 101-105 at a particular instant is bent with, say, a force of 0.1 N, as the corresponding finger 11-15 is currently pressed against a particular surface, does not constitute a "program" in the present sense. Instead, a "program" rather prescribes how to calculate an appropriate bending force (or any other actuating means 240 control parameter) based upon a given set of measurement data from the sensor means 210, producing variable control parameters based upon variable input data, according to a certain set of logical rules. Hence, under one particular program, different actuating means 240 control will typically result based upon different input sensor means 210 data. Two programs may also differ by, for instance, taking differently into consideration different input values, or only feeding control information to different actuating means.

Herein, the term "measurement location" refers to a location where the said force is measured using the sensor means 210. Such a measurement location may be point-like or have a certain surface extension.

A "pattern" as used herein refers to a particular combination of measurement data from the sensor means 210, preferably but not necessarily including data from all of said measurement locations, and possibly also one or several predetermined finger 101-105 positions and/or angles, as measured for example by the control device 230 measuring the longitudinal position of respective tendons 250. Such a "pattern" may be defined in terms of absolute force values, such as "measurement locations 213 and 215 measuring force values of at least 35 [units] simultaneously", and/or relative force values, such as "measurement location number 218 measuring a force value which is at least double the force value simultaneously read from any other measurement location 211-217". The pattern may also involve a time dependence, such as "measurement location number 213 measuring a force value which is first raised to at least 5 times as much as an original value, then again is decreased at least back to original level, followed by measurement location number 211 being raised to a level of at least 5 times, then again being decreased at least back to original level". It is preferred, but not necessary, that the pattern comprises not only measurement data from only one measurement location, but from at least two different measurement locations.

According to a very preferred embodiment, the said pattern comprises measurement values from at least one measurement location the measurement value of which is used as an input parameter into said first control program during its normal use. Preferably, all measurement locations 211-218 are such measurement locations, being used in the first control program. In other words, it is preferred that no measurement location used in the said pattern is a measurement location the only function of which is to trigger the detection of said pattern. In other words, there is for instance no peripherally arranged button for manually switching to a particular control state, thereby starting a particular program, which button does not take part in the general gripping-enhancing program of the glove 100.

According to a preferred embodiment, the triggering pattern comprises, in addition to said sensor measurement values, a measured angle or position of at least one glove 100 finger 101-105, as measured by the control device 230. For instance, in order for the triggering pattern to be detected, in addition to a certain predetermined pattern of sensed force measurement values from the sensor means 210, the control device 230 must sense one or several particular glove 100 fingers 101-105 to be in a respective particular predetermined position or angle, such as "at least 25% from a fully extended position towards a gripping position".

Using such a control system 200 and such a glove 100, particular second control programs can hence be implemented and triggered by the user activating corresponding patterns using the glove 100 itself. In particular, since the force sensor means 210 used during normal force strengthening use of the glove may be used to trigger such second control programs, several advantages accrue.

Firstly, there is no need for external or additional control interface components, arranged to trigger the switch to such second control states and hence triggering such second control programs.

Secondly, patterns may be defined so as to allow a user of the glove 100 to be able to perform particular chores by quickly and naturally activating corresponding patterns in ways that are not only ergonomically sound, but also intuitive depending on the particular situation. This provides for a glove 100 which is not only more comfortable and ergonomic to use, but which also provides more efficient and flexible aid to the user across a much broader spectrum of circumstances than has previously been the case.

Thirdly, since the pattern detection and second program logic can easily be implemented in the control device 230, for instance by a simple software update, such improved functionality can be implemented in a very quick, easy and inexpensive manner. Also, the functionality can be updated continuously as the needs of the user change over time, or even to, on the fly, cater for the current needs of a user in a particular temporary situation.

Below, preferred examples of such patterns and second control programs will be presented, in particular in connection to FIGS. 3a-4c.

As described above, the said pattern is constituted by a particular predetermined type of combination of measurement values, as measured by the sensor means 210 at particular respective measurement locations 211-218. It is realized that the sensor means 210 may be in the form of one and the same sensor, arranged to measure pressure and/or force at several such locations 211-218, even along a continuous surface, of the glove 100 fingers 101-105. However, it is preferred that the sensor means 210 comprises at least two distinct force sensors, in turn arranged at said respective measurement locations 211-218 and connected to a central processing unit, or directly to the control device 230. In the figures, the sensor means 210 comprises one such respective sensor for each measurement location 211-218.

As implied above, there may be several different second programs, the corresponding second control state of each is activated by at least one particular respective triggering pattern. What is said herein in relation to the second control state and program is in general valid also for such several individual second control states and programs.

Preferably, the above mentioned first program is arranged to implement the said feedback loop as described above, possibly in a way which is conventional as such.

In general, the second program may furthermore be similar to the first program, in that the second program defines an algorithm using which, based upon measurement values read by the sensor means 210, the actuating means 240 is controlled so as to achieve a particular purpose in a particular use case as triggered by said detected pattern. For some second programs, the control of the actuating means 240 may, however, be independent of the measured force values. In all cases, the algorithm is different between the first and the second programs.

More particularly, according to a preferred embodiment, the second program may comprise the bending of at least one finger to a predetermined respective bending position, and then (when said bending position has been reached, for instance as measured internally in the control device 230, using its normal, existing functionality), holding the glove 100 finger 101-105 in question still in the predetermined bending position. This may pertain to several respective fingers 101-105, and may for instance be used as a part of a second control program for holding a heavy object in a certain orientation, or for carrying a bag as described in detail below.

In another preferred embodiment, the second program comprises applying a predetermined respective bending force to at least one glove 100 finger 101-105, for instance irrespectively of the current bending position of the finger 101-105 in question. The predetermined bending force may be predetermined in terms of an absolute force or a relative force, such as in relation to a currently detected corresponding force measurement value, By way of example, this type of second program can be used to impart super-normal strengthening to one or several particular fingers under certain circumstances, as compared to under the regime of the first program.

These examples of second program features may be combined freely, for same or different fingers. The same is true for a third preferred example, according to which the second program comprises maintaining the current bending position of at least one glove 100 finger 101-105 by applying a counter force resisting an externally applied bending force of the glove 100 finger 101-105 when and if such an externally applied bending force is present. Such a force may be detected and measured using the normal, existing internal functionality of the control device 230.

In particular, in order to achieve this maintaining in a simple manner, it is preferred that the control device 230 comprises a self-locking driving device, and that the said maintaining of the current bending position of the glove 100 finger 101-105 is achieved by the power to the said driving device simply being switched off. One example of such self-locking driving device is one in which a pulling and/or pushing force is generated, and applied to a respective glove 100 finger 101-105, using a pushing/pulling screw actuated by a worm drive. Then, the thread pitch of the worm drive, and so forth, is selected so that an external longitudinal force applied on the said screw will not move the worm drive.

The actuating means 240 may comprise stiff bars and joints, such as in an exoskeleton type structure. See DE102012002785A1 for an example of this. However, the above described self-locking functionality is particularly useful in the preferred case illustrated in the figures, in which the actuating means 240 operating on at least one glove 100 finger 101-105 comprises a respective artificial tendon 250 connected to the glove 100 finger 101-105 in question, at respective fastening points 255, which tendon 250 is arranged to bend the finger 101-105 in question by the control device 230 applying a respective pulling force to the respective tendon 250 and as a result also to the glove 100 finger 101-105 in question. The tendon can be attached to the control device 230 via conventional Bowden cables 330. In this case, the actuating means may simply comprise a self-locking mechanism such as the worm driven screw described above, which is used to impart said pulling force and to adjust the length of the tendon 250 in question. The fastening points 255 may also provide a respective slidable engagement with the tendons 250.

Only one first or second program can be used by the control device 230 at any one time. Hence, when the said pattern is detected, the control device 230 switches from the first to a second control state, in other words stops using the first program for controlling the actuating means 240, and instead starts using the said second program corresponding to the said pattern. Preferably, this second program is then used until a certain criterion is fulfilled, at which point either the first control state, and hence the first control program, is again used, or another second state, with corresponding second program, is used.

For instance, the criterion may be that another triggering pattern is detected, corresponding to another second control state, in which case this other second program is started, preferably immediately.

Another criterion may be that the triggering pattern associated with the used second state is no longer detected. In other words, when the control device 230 is in the second control state, the control device 230 is arranged to detect the disappearance of the predetermined triggering pattern. The second program can be disengaged, and the first program again started, immediately upon such detection of the disappearance of the pattern. However, preferably, the second program is disengaged and the first program is again started only after the predetermined triggering pattern has not been read from said sensor means during a predetermined time period, which preferably is at least 1 seconds, more preferably at least 3 seconds, in some preferred cases at least 10 seconds. This is hence a timeout functionality, allowing the user to rest his or her hand, or the like, during a certain short timeout period, before the functionality of the second program is stopped as a consequence.

Another criterion may be that the control device 230 is arranged to detect a predetermined release pattern, which is similar to the above described triggering patterns, but associated with a release instruction or with the initiation of the first program. Hence, the release pattern is a pattern of measurement values at respective measurement locations 211-218 as measured by said sensor means 210, and as detected by the control device 230 when it is in the second control state. In this case, the control device 230 is preferably arranged so that, when the said release pattern is detected, it immediately switches to control the actuator means 240 according to the first program again. Such a release pattern may hence be used to, for instance, override the above described timeout functionality. Even though different control states may be associated with different such control patterns, each arranged to be easily reachable and/or ergonomic in the situation in which the particular second program is intended to use, it is preferred that one and the same release pattern is common to all second programs implemented by the control device 230.

In the following, a number of specific examples of preferred second programs will be described with reference to the figures.

FIG. 3a shows the glove 100 on the human hand 10, wherein the user carries a bag by its handle 20. In this case, the second program is initiated by the control device 230 detecting a triggering pattern illustrated in FIG. 3b using a filled circle. When the measurement location 216 reports a force above a certain threshold value, and the other measurement locations 211-215; 217-218 report respective forces below certain respective other threshold values, the control device 230 hence initiates the second program. In this case, a bending of a particular finger, such as for instance a detected bending of the finger 13 beyond a predetermined bending angle, may also be part of the triggering pattern.

Then, the second program is arranged so that the control device 130 is caused to drive one of several fingers, such as fingers 13 and 14 or fingers 13, 14 and 15, to a bending position adapted for holding the handle 20 of a bag, a suitcase or a similar carried article, possibly using a predetermined bending force BF. In addition, the second program is arranged so that the control device 230 is thereafter caused to apply a counter force CF resisting a finger straightening force applied by the handle 20 to the said one or several fingers 13, 14 or 13, 14, 15.

In this particular example, as well as generally, it is preferred that, when the control device 230 is in the first control state, the counter force CF resisting the said finger straightening force is not applied.

Hence, in this example, the user places the handle 20 on the measurement location 216 and raises the hand 10. Then, the measurement location 216 will report a certain pressure, as a result of which the second program is initiated, causing the glove 100 to grip the bag handle 20 for carrying.

The example illustrated in FIGS. 3a and 3b shows a preferred aspect of the invention, namely according to which the triggering pattern corresponds to a sensor means 210 measurement pattern normally read by the sensor means 210 when the human hand 10 performs a particular gripping action in relation to a particular object 20 while wearing the strengthening glove 100, which action is strengthened, aided or maintained by the second program in a way which would not result when the control device 230 is in the first control state. Hence, the gripping by fingers 13, 14, 15 according to the first program, that is the normal finger strengthening feedback loop, would not bend these fingers to the respective predetermined position, neither impart the counter force CF at this respective position, as a result of the measurement location 216 reporting the above described pressure.

FIGS. 3a and 3b also serve to illustrate a preferred embodiment, according to which the said triggering pattern comprises a first group of at least one specific of said measurement locations 211-218, a respective measurement value of each representing a respective force which is significantly stronger, preferably at least 10 times stronger, than all measurement values of a second group of at least one specific of said measurement locations 211-218, which first and second groups are disjoint with respect to measurement locations. In FIG. 3b, the first group comprises only location 216, which the other locations 211-215; 217-218 are comprised in the second group.

Hence, the first group comprises a measurement location 216 arranged on the glove finger 103 corresponding to the proximal phalange of the long finger 13. As an alternative, it would be possible to also use a measurement location (not shown) arranged at the proximal phalange of the ring finger 14 in the said first group.

The said first group may alternatively comprise only one or several measurement locations (not shown) arranged on the intermediate phalanx of the glove finger 204 corresponding to the ring finger 14 of said human hand; or only one or several measurement locations (not shown) arranged on the ulnar side of the glove finger 204, 205 corresponding to the ring 14 or little 15 finger of the said human hand 10.

FIGS. 4a-4c illustrate a second example of a second program according to the present invention, in which the user is aided in a gripping of a bar-like structure 30 of a certain diameter, such as the handle of a vacuum cleaner or a handlebar in a bus. In this case, as illustrated in FIG. 4b, a first group of measurement locations comprises locations 212 and 214, arranged at the base of the thumb 11 and index finger 12 glove 100 finger 101, 102, respectively. When these locations 212, 214 report a certain minimum pressure to the control device 230, and the other locations 211; 213-218 do not, the triggering pattern is detected and the second program illustrated in FIG. 4a is initiated. The triggering pattern may also comprise the detected bending of one or more glove 100 fingers, such as fingers 103 and/or 104.

Alternatively, the activation program may involve a measurement location (not shown) arranged on the palm 106 of the glove 100.

The second program, in this example, comprises bending of the fingers 103 and 104, and preferably also finger 105, until fully bent or until not being able to bend anymore due to the resistance of the structure 30, and then to apply a bending force BF to hold on to the structure 30.

It is in this case preferred that the triggering pattern also comprises a time aspect, in the sense that the triggering pattern is not detected until the said force pattern has been detected uninterruptedly over a particular time period, such as at least 1 second. Preferably, a certain minimum bending of the fingers 103, 104 and 105 must also be detected throughout this time period in order for the triggering pattern to be detected.

As described above, for both examples 3a-3b; 4a-4c, the respective second program may be stopped as a result of the corresponding triggering pattern no longer being detected. As an alternative, or in addition to this, it is preferred that a release pattern may be detected by the control device 230. FIG. 4a illustrates an example of such release pattern, in which the index glove 100 finger 102 is moved or waved in a "waving" direction WD, possibly during a predetermined minimum time period. As the user performs this movement, the second program is immediately dropped by the control device 230, and the normal feedback loop is again performed. For such a release pattern involving a position and/or movement of one or several particular fingers, it is preferred that the involved finger or fingers do not hold any of the measurement locations 211-218 in the said first group, and also that the second program does not involve controlling the said involved finger or fingers in a way prohibiting the user from performing the release pattern movements.

The release pattern illustrated in FIG. 4c may also be used in the example illustrated in FIGS. 3a-3b. An alternative release pattern is shown in FIG. 5, according to which measurement locations 211 and 213, at the tip of the thumb 101 and index finger 102, respectively, of the glove 100 form a group similar to the first group discussed above. When these measurement locations 211, 213 simultaneously report a respective pressure which increases at least as quickly as a predetermined value, the second program is immediately released. Such simultaneous pressure increase may, for instance, be imparted by the user pressing together the thumb 11 tip to the index finger 12 tip.

A third example, which is not shown in the figures, is an assembly sequence aiding function, in which the second program comprises imparting a strong grip during a certain predetermined time period, followed by full opening of the glove 100. In this case, the corresponding triggering pattern may comprise detecting, via suitable measurement locations, the holding of a particular object in a particular orientation followed by one or a couple of light detected pressure peaks.

Many more second control programs, with corresponding intuitive triggering patterns, are thinkable, for many different and diverse applications.

FIG. 6 illustrates the method steps of a method according to the present invention for operating a strengthening glove 100 of the type described above.

In a preferred step 301, the glove 100 is provided, comprising the control system 200. This step may comprise providing the glove 100 to a user. In connection thereto, or at a later point, in a step 302 the control device 230 enters the above described first control state, why the above described first control program is initiated, and as a result the glove 100 functions for automatically strengthening the grip of the user, as described above.

In a step 303, the control device 230 reads the measurement values from the sensor means 210, also as described above, while in said first control state. In a step 304, the control device 230 detects the above-described predetermined triggering pattern of the measurement values, and, if the measured values correspond to the triggering pattern, the control device 230 automatically switches to the second control state, whereby the second control program is automatically initiated, in a step 306. Otherwise, the control device 230 remains in the first control state and, in a step 305, causes the actuating means 240 to be controlled according to the first program, providing said automatic feedback strengthening of the user's hand 10, after which the method iterates back to step 303.

In a step 307, similar to step 303 while the control device 230 is in the second control state, the sensor means 210 measurement values (from the same measurement locations as in step 303) are again read by the control device 230.

Again, in a step 311, since the triggering pattern was detected in step 304, the control device 230 is caused to control the actuating means 240 according to a corresponding second control program. Thereafter, the method iterates back to step 307.

The control device 230 can switch back to the first control state, or to another second control state, and control according to the second program can hence stop, when at least one of one or several predetermined criteria is met, as described above.

Namely, in a step 308 the control device 230 is arranged to, while in said second control state, determine whether the read measurement values correspond to the above described release pattern, and, if this is the case, the method proceeds to a step 312, in which it switches back to the first control state and the first program is as a result again initiated, after which the method iterates back to step 303.

In a step 309, the control device 230 is arranged to, while in the second control state, determine whether the read measurement values still correspond to the said triggering pattern detected in step 304. If this is the case, the method proceeds to step 311. If not, in a step 310, it is checked whether a timeout period has expired since the triggering pattern was last detected, and if this is the case the method proceeds to step 312.

It is realized that the method illustrated in FIG. 7 is one of many possible examples of such an operating method. For instance, if several different triggering patterns are arranged to spawn several different respective control states/programs, the step 304 may comprise several possible branches, depending on which one of said triggering patterns was detected. Likewise, in step 308, a different triggering pattern may be detected, after which, in step 312 a corresponding second control state may be initiated rather than the first control state.

Above, a number of exemplifying embodiments have been described. However, it is apparent to the skilled person that many modifications may be made to these embodiments without departing from the basic idea of the invention.

For instance, measurement locations may be placed at different locations than the ones shown in the figures.

Activation patterns may also be used to trigger other functionality than the control device 230 controlling the glove 100 according to what has been described above. One example of this is that the control device 230 detects that the user waves the hand 10, which triggers the control device 230 to switch the glove 100 off completely. Other activation patterns may trigger the control device 230 to communicate a battery status to the user, or to activate a wireless communication functionality, such as using Bluetooth® technology.

In general, the above described examples are freely combinable as applicable.

Hence, the invention is not limited to the said embodiments, but can be varied across the full scope of the enclosed claims.

The invention claimed is:

1. Control system for a strengthening glove with at least one glove finger, the control system strengthening a gripping movement performed by a human hand wearing the glove, which control system comprises:
   at least one force detecting sensor means that detects, in at least two different measurement locations on a palm side of said at least one glove finger, a respective force between a respective human finger wearing the respective glove finger and a respective contact surface onto which said gripping movement is applied,
   at least one actuating means that imparts a force to a respective one of said glove fingers, so that the corresponding human finger wearing the glove finger to which the force is applied is bent towards a gripping position, and
   a control device that reads a respective measurement value from the sensor means for each of said measurement locations, and controls the respective force applied by said at least one actuating means using a force strengthening feedback loop based upon the said measurement values,
   wherein the control device operates in a first control state and controls the actuating means according to a first program when a predetermined pattern of measurement values is not detected, and switches to a second control state and controls the actuating means according to a second program when the predetermined pattern of the measurement values is detect,
   wherein the first and second programs are different, and
   wherein the predetermined pattern corresponds to a pattern read by the sensor means for a particular gripping action in relation to a particular object.

2. Control system according to claim 1, wherein the pattern comprises, in addition to said measurement values, a measured angle or position of at least one glove finger.

3. Control system according to claim 1, wherein the first program is arranged to implement the said feedback loop.

4. Control system according to claim 1, wherein the actuating means of at least one glove finger comprises a respective tendon connected to the glove finger in question, which tendon is arranged to bend the finger in question by the control device applying a pulling force to the tendon and as a result also to the glove finger in question.

5. Control system according to claim 1, wherein the said pattern corresponds to a pattern normally read by the sensor means when the human hand performs a particular gripping action in relation to a particular object while wearing the strengthening glove, which action is strengthened, aided or maintained by the second program in a way which would not result when the control device controls the actuating means according to the first program.

6. Control system according to claim 1, wherein the measurement values being comprised in said pattern correspond to a first group of at least one specific of said measurement locations, a respective measurement value of each representing a respective force which is significantly stronger, preferably at least 10 times stronger, than all measurement values of a second group of at least one specific of said measurement locations, which first and second groups are disjoint with respect to measurement locations.

7. Control system according to claim 1, wherein the control device is arranged to detect a predetermined release pattern comprising measurement values from said sensor means when in said second control state, and in that the control device is arranged so that, when the said release pattern is detected, it immediately switches back to the first control state.

8. Control system according to claim 1, wherein the predetermined pattern is at least partly defined in terms of a time dependence of measurement values.

9. Control system according to claim 1, wherein the control device is arranged to, when in said second control state, detect the disappearance of the said predetermined pattern, and as a result switch back to the said first control state.

10. Control system according to claim 9, wherein, when the control device is arranged to, when in said second control state, detect the disappearance of the predetermined pattern only after the predetermined pattern has not been read from said sensor means during a predetermined time period, which preferably is at least 1 seconds.

11. Control system according to claim 1, wherein the sensor means comprises at least two distinct force sensors, each arranged at said respective measurement locations.

12. Control system according to claim 11, wherein the second program comprises applying a predetermined respective bending force to at least one finger.

13. Control system according to claim 1, wherein the second program comprises the bending of at least one finger to a predetermined respective bending position and then holding the finger in the predetermined bending position.

14. Control system according to claim 13, wherein the second program comprises bending one or several fingers to a bending position adapted for holding the handle of a bag, a suitcase or a similar carried article, and to then apply a counter force resisting a finger straightening force applied by the handle to the said one or several fingers.

15. Control system according to claim 14, wherein, when the control device controls the actuating means according to the first program, the said counter force resisting the said finger straightening force is not applied.

16. Control system according to claim 1, wherein the second program comprises maintaining the current bending position of at least one finger by applying a counter force resisting an externally applied bending force of the finger when such an externally applied bending force is present.

17. Control system according to claim 16, wherein the control device comprises a self-locking driving device, and wherein the said maintaining of the current bending position is achieved by the power to the driving device simply being switched off.

18. Strengthening glove comprising a control system according to claim 1 for strengthening a gripping action of a human hand wearing the glove.

19. Method for operating a strengthening glove with at least one glove finger, which glove is arranged to strengthen a gripping movement performed by a human hand wearing the glove, which glove comprises at least one force detecting sensor means arranged to detect, in at least two different measurement locations on the palm side of said at least one glove finger, a respective force between a respective human finger wearing the respective glove finger and a respective contact surface onto which said gripping movement is applied, which glove further comprises at least one actuating means arranged to impart a force to a respective one of said glove fingers, so that the corresponding human finger wearing the glove finger in question is bent towards a gripping position, which glove further comprises a control device, arranged to read a respective measurement value from the sensor means for each of said measurement locations and to control the respective force applied by said at least one actuating means using a force strengthening feedback loop based upon the said measurement values, wherein the method comprises the steps of:
   a) detecting a predetermined pattern of the measurement values;
   b) operating in a first control state and controlling the actuating means according to a first program when the predetermined pattern of measurement values is not detected; and
   c) switching to a second control state and controlling the actuating means according to a second program when the predetermined pattern of the measurement values is detected,
   wherein the first and second programs are different, and
   wherein the predetermined pattern corresponds to a pattern read by the sensor means for a particular gripping action in relation to a particular object.

20. Method of claim 19, wherein the predetermined pattern is at least partly defined in terms of a time dependence of measurement values.

* * * * *